(12) United States Patent
Maldonado et al.

(10) Patent No.: US 9,259,024 B2
(45) Date of Patent: Feb. 16, 2016

(54) HIGH CALORIC ENTERAL FORMULATIONS

(75) Inventors: Yadilka Maldonado, Dardenne Prairie, MO (US); William C. Smith, Cahokia, IL (US); Minhthy Nguyen, Sunset Hills, MO (US)

(73) Assignee: SOLAE LLC, St. Louis, MO (US)

( * ) Notice: Subject to any disclaimer, the term of this patent is extended or adjusted under 35 U.S.C. 154(b) by 1204 days.

(21) Appl. No.: 13/122,574

(22) PCT Filed: Oct. 12, 2009

(86) PCT No.: PCT/US2009/060384
§ 371 (c)(1),
(2), (4) Date: Apr. 5, 2011

(87) PCT Pub. No.: WO2010/042932
PCT Pub. Date: Apr. 15, 2010

(65) Prior Publication Data
US 2011/0183900 A1   Jul. 28, 2011

Related U.S. Application Data

(60) Provisional application No. 61/104,554, filed on Oct. 10, 2008.

(51) Int. Cl.
*A23L 1/29* (2006.01)
*A23L 1/305* (2006.01)

(52) U.S. Cl.
CPC .............. *A23L 1/296* (2013.01); *A23L 1/3053* (2013.01); *A23L 1/3055* (2013.01); *A23V 2002/00* (2013.01)

(58) Field of Classification Search
None
See application file for complete search history.

(56) References Cited

U.S. PATENT DOCUMENTS

| 5,547,927 | A | 8/1996 | Cope et al. | |
|---|---|---|---|---|
| 2001/0043958 | A1 * | 11/2001 | McEwen et al. | 424/757 |
| 2005/0220979 | A1 * | 10/2005 | Baumer et al. | 426/656 |
| 2006/0134310 | A1 | 6/2006 | Cho et al. | |

FOREIGN PATENT DOCUMENTS

| EP | 0626177 | * | 12/1999 |
|---|---|---|---|
| EP | 1236405 | | 9/2002 |
| WO | 9402166 | | 2/1994 |
| WO | WO 94/02166 | * | 2/1994 |
| WO | 9956564 | | 11/1999 |
| WO | 2008131008 | | 10/2008 |

OTHER PUBLICATIONS

Lamsal, et al. "Rheological Properties of Soy Protein Hydrolysates Obtained from Limited Enzymatic Hydrolysis." Lebensmittel Wissenschaft Und Technologie, Academic Press, London, GB, vol. 40, No. 7, 26 Apr. 1, 2007, pp. 1215-1223, XP022056234 ISSN: 0023-6438.
Federal Register/vol. 79, No. 241/Tuesday, Dec. 16, 2014/Rules and Regulations, pp. 74618-74633.

* cited by examiner

*Primary Examiner* — Satyanarayana R Gudibande (57) ABSTRACT

Compositions and methods relating to high caloric enteral formulations are disclosed herein. The invention provides a dietary composition comprising hydrolyzed soy protein and having a low viscosity and acceptable shelf life. Methods of using the dietary compositions of the invention are also disclosed.

17 Claims, 2 Drawing Sheets

HIGH CALORIC ENTERAL FORMULATIONS

CROSS REFERENCE TO RELATED APPLICATIONS

This application claims the priority of U.S. Provisional Application No. 61/104,554 filed Oct. 10, 2008, which is hereby incorporated by reference in its entirety.

FIELD OF THE INVENTION

The present invention relates to dietary compositions and methods useful for enteral feeding. In particular, the invention includes high caloric enteral feeding formulations having low viscosity and acceptable stability.

BACKGROUND OF THE INVENTION

Enteral feeding formulations can be high caloric density products developed to meet nutritional requirements of subjects under metabolic and/or physiological stress. Such subjects include those suffering from traumatic injury, burns, post-surgery, and some disease states that have a significant need for increased nutrients and energy as compared to subjects who are not challenged by such metabolic and/or physiological stressors. Nutrients that a subject can typically synthesize in adequate supply may become limiting when challenged by a metabolic and/or physiological stress. Further, absorption of nutrients from the gastrointestinal tract can be compromised even when there is no direct injury to the gastrointestinal system.

Subjects faced with metabolic and/or physiological challenges are often fed either with parenteral formulations or enteral formulations to replace or supplement a typical diet. These products can deliver between 1.0-2.0 kcal/ml and are typically formulated with high biological value protein like casein and soy proteins. When these formulations are provided through tube feeding, they are administered by gravity or using a pump requiring a particular viscosity and stability for the duration of the feeding regiment.

The caloric capacity of numerous enteral feeding formulations is limited by the increase in viscosity associated with the inclusion of dairy and soy protein ingredients. Enteral feeding formulations containing dairy and soy protein ingredients exhibit high initial viscosity or viscosity build-up over time as the inclusion level of these ingredients increases. The elevated viscosity results in a thicker product that affects the flow rate of the enteral feeding formulation to the subject. Enzyme-treated dairy and soy protein ingredients have helped to alleviate the viscosity challenges; however, stability issues such as sedimentation, flocculation, and phase-separation arise when significant inclusion levels of enzyme-treated proteins are used in formulations destined for significant terminal sterilization of the enteral products. Accordingly, there is a need for an enteral feed formulation having a high caloric content, low viscosity, and stability throughout the shelf life.

SUMMARY

The present invention provides compositions and methods relating to a dietary composition having a caloric density of about 1.3 kcal/ml to about 2.1 kcal/ml and a low viscosity ranging from between about 30 and about 200 centipoises. The composition includes enzymatically hydrolyzed soy protein material, which has a degree of hydrolysis of between about 0.1% and about 16%, preferably between about 0.1 and about 5% when hydrolyzed soy protein is the only protein in the composition. The composition further includes a carbohydrate source, a lipid source, and necessary micronutrients (vitamins and minerals) for the particular end use application. While not required, the composition may include 100% or more of the United States Reference Daily Intake (US RDI) of vitamins and minerals. The composition may include nutrients within the minimum and the maximum range of the EU Foods for Special Medical Purposes (EU FSMP) requirements for a particular end use application. The composition is provided as a liquid and administered enterally. Also, the composition retains stability characteristics following terminal sterilization.

Another aspect of the invention provides methods of using the compositions of the invention. A method of providing nutrition to a subject in need thereof is provided. The method includes administering to the subject a formulation having an enzymatically hydrolyzed soy protein material, which has a degree of hydrolysis of between about 0.1% and about 16%, preferably between about 0.1 and about 5%. The composition may be administered enterally or through other means delivering the composition to the gastrointestinal tract.

DETAILED DESCRIPTION

The present invention provides compositions and methods useful for providing nutrition to metabolically and/or physiologically stressed subjects. It has been discovered, as demonstrated in the examples, that enteral feed formulations containing specifically treated soy protein results in a formulation having an adequate and/or high caloric content with low viscosity and acceptable shelf life stability. Specifically, the soy protein is enzymatically treated to a degree of hydrolysis that ranges between about 0.1 and about 16% preferably between about 0.1% and about 5%.

I. Composition

The present invention provides a composition that is directed to meet the nutritional needs of metabolically and/or physiologically stressed subjects. The composition can be calorically dense, while at the same time having low viscosity and acceptable shelf life stability. The formulation of the invention preferably utilizes hydrolyzed soy protein.

The protein source of the present invention provides between about 14% and about 25% of the total calories of the composition, preferably between about 15% and about 20%.

The composition of the present invention is preferably a hydrolyzed protein-based diet. In choosing the protein source, the present invention maximizes tolerance and absorption with the use of a hydrolyzed protein. In one aspect of the invention, the protein source is enzymatically hydrolyzed soy protein. The protein source may be hydrolyzed soy protein, soy protein, casein, whey, hydrolyzed casein, hydrolyzed whey, and combinations thereof.

(a) Soy Protein Material

Soy protein products have a high protein content and low oligosaccharide/carbohydrate content. Further, soy protein products provide a "complete" protein. Soybeans contain all of the amino acids essential to human nutrition, which must be supplied in the diet because they cannot be synthesized by the human body. In addition to their high protein/low carbohydrate content, soy proteins contain no cholesterol. For decades, nutritional studies have indicated that the inclusion of soy protein in the diet actually reduces serum cholesterol levels in people who are at risk. Further, the higher the blood cholesterol level, the more effective soy proteins are in lowering that level.

Generally, a variety of soy protein materials may be used in the process of the invention to generate a soy protein hydrolysate. The soy protein material may be derived from whole soybeans in accordance with methods known in the art. The whole soybeans may be standard soybeans (i.e., non genetically modified soybeans), genetically modified soybeans (such as, e.g., soybeans with modified oils, soybeans with modified carbohydrates, soybeans with modified protein subunits, and so forth) or combinations thereof. Suitable examples of soy protein material include, without limitation, soy extract, soy curd, soy flour, soy protein isolate, soy protein concentrate, powdered or dry soy milk, soy meal, ground soy bean, soy bean paste, and mixtures thereof. Additional suitable soy protein materials for use with the invention include soy flakes, soy flour, soy grits, soy meal, soy protein concentrates, isolated soy proteins, and mixtures thereof. The primary difference between these soy protein materials is the degree of refinement relative to whole soybeans.

Soy flakes are generally produced by dehulling, defatting, and grinding the soybean and typically contain less than about 65% (by weight) soy protein on a moisture-free basis. Soy flakes also contain soluble carbohydrates, insoluble carbohydrates such as soy fiber, and fat inherent in soy. Soy flakes may be defatted, for example, by extraction with hexane. Soy flours, soy grits, and soy meals are produced from soy flakes by comminuting the flakes in grinding and milling equipment such as a hammer mill or an air jet mill to a desired particle size. The comminuted materials are typically heat treated with dry heat or steamed with moist heat to "toast" the ground flakes and inactivate anti-nutritional elements present in soy such as Bowman-Birk and Kunitz trypsin inhibitors. Heat treating the ground flakes in the presence of significant amounts of water is avoided to prevent denaturation of the soy protein in the material and to avoid costs involved in the addition and removal of water from the soy material. The resulting ground, heat treated material is a soy flour, soy grit, or a soy meal, depending on the average particle size of the material. Soy flour generally has a particle size of less than about 150 μm. Soy grits generally have a particle size of about 150 to about 1000 μm. Soy meal generally has a particle size of greater than about 1000 μm.

Soy protein concentrates typically contain from about 65% (by weight) to less than about 90% (by weight) soy protein on a moisture-free basis, with the major non-protein component being fiber. Soy protein concentrates are typically formed from defatted soy flakes by washing the flakes with either an aqueous alcohol solution or an acidic aqueous solution to remove the soluble carbohydrates from the protein and fiber. Examples of suitable soy protein concentrates include Promine DSPC, Procon, Alpha® 12, and Alpha® 5800, which are available from Solae, LLC (St. Louis, Mo.). Further, soy protein concentrate may be blended with the soy protein isolate to substitute for a portion of the soy protein isolate as a source of soy protein material. Typically, if a soy protein concentrate is substituted for up to about 40% of the soy protein isolate by weight, at most, and more preferably is substituted for up to about 30% of the soy protein isolate by weight.

Soy protein isolates, also referred to as isolated soy proteins, which are more highly refined soy protein materials, are processed to contain at least about 90% (by weight) soy protein on a moisture-free basis and little or no soluble carbohydrates or fiber. Isolated soy proteins are typically formed by extracting soy protein and water soluble carbohydrates from defatted soy flakes or soy flour with an alkaline aqueous extractant. The aqueous extract, along with the soluble protein and soluble carbohydrates, is separated from materials that are insoluble in the extract, mainly fiber. The extract is typically then treated with an acid to adjust the pH of the extract to the isoelectric point of the protein to precipitate the protein from the extract. The precipitated protein is separated from the extract, which retains the soluble carbohydrates, and is dried after an optional pH adjustment step. The soy protein isolate may comprise intact soy proteins or it may comprise partially hydrolyzed soy proteins. Exemplary commercially available soy protein isolates include SUPRO® 500E, SUPRO® 545, SUPRO® 670, SUPRO® Plus 675, SUPRO® 760, SUPRO® 620, SUPRO® EX33, SUPRO® 8020, and SUPRO® 8021 (Solae, LLC, St. Louis, Mo.).

The composition of the invention includes a hydrolyzed soy protein material. The degree of hydrolysis (DH) refers to the percent of specific peptide bonds that are hydrolyzed (that is, the number of cleaved out of the number of peptide bonds present in the intact protein). A low degree of hydrolysis includes less than about 16% DH. The DH may be about 0.1, 0.5, 1.0, 1.5, 2.0, 2.5, 3, 4, 5, 6, 7, 8, 9, 10, 11, 12, 13, 14, 15, or 16%. Preferably, the DH is between about 0.1% and about 5%. The process involves contacting a soy protein material with an endopeptidase that cleaves the soy protein material to produce a protein hydrolysate containing a mixture of small and large polypeptide fragments.

Hydrolysis may be carried out using a suitable peptidase. Such peptidases include, but are not limited to, those of the serine endopeptidase family isolated from *Bacillus subtilis*. Representative alkaline proteases suitable for use in the processes of the present invention include *Fusarium* trypsin-like endopeptidase (TL1) (U.S. Pat. No. 5,255,627, U.S. Pat. No. 5,693,520, each of which is hereby incorporated by reference in its entirety). ALCALASE® (Novozymes A/S, Denmark); Alkaline Protease Concentrate (Valley Research, South Bend, Ind.); and Protex™ 6 L (Genencor, Palo Alto, Calif.), Bacteria Alkaline Protease. Preferably, the endopeptidase TL1 may be used to produce soy protein polypeptides with a DH between about 0.1% and about 16%.

Soy protein material that has a low degree of hydrolysis (DH) typically also has a high average molecular weight. The degree of hydrolysis refers to the percent of specific peptide bonds that are hydrolyzed. Hydrolyzing soy protein material to a low DH may be reached by carrying out hydrolysis until the range of between about 0.1% and about 16% DH. Methods for measuring DH are well known in the art. A skilled artisan may use, for example, the trinitrobenzene sulfonic acid (TNBS) method or the pH-STAT method (Jacobsen, C. F., et al. "Methods of Biochemical Analysis", Vol. IV, pp. 171-210, Interscience Publishers Inc., New York (1957)).

The soy protein material may be hydrolyzed using any means known in the art. For example, the soy protein material may be hydrolyzed using an enzyme treatment, heat treatment, or acid/alkali treatment during processing of the soy protein material. Particularly preferred for hydrolysis of the soy protein material for use in the present disclosure is an enzyme treatment. In particular is the enzyme treatment described in US Patent Application 2008/0305212, and incorporated herein by reference in its entirety.

Generally, the process for the enzyme hydrolysis of the soy protein material comprises diluting the soy protein material with water to form a soy protein slurry and adjusting the pH of the soy protein slurry to an alkaline pH with a suitable base.

This is followed by heat-treating the pH-adjusted soy protein slurry and reacting the pH-adjusted soy protein slurry with an enzyme with or without maintaining the pH level to form an enzyme hydrolyzed soy protein mixture. The resulting enzyme hydrolyzed soy protein mixture is the soy protein material. Additional optional steps are described in more detail below.

In the first step described above, the soy protein material is diluted with water to form a soy protein slurry. Suitably, the soy protein material is diluted with water to produce a soy protein slurry that is between about 1% and about 20% solids, by weight on an "as is" basis. Still more suitably, the soy protein slurry is between about 16% and about 20% solids, by weight on an "as is" basis, and even more suitably, between about 11% and about 15% solids, by weight on an "as is" basis.

The pH of the soy protein slurry is then adjusted to a pH of between about 6.0 and about 11.0 with a suitable base. More suitably, the pH of the soy protein slurry is adjusted to between about 7.0 and about 9.0. Suitable bases include sodium hydroxide, potassium hydroxide, and mixtures thereof. Preferably, the pH of the soy protein slurry is adjusted with sodium hydroxide.

The pH-adjusted soy protein slurry is then heat-treated. Preferably, the pH-adjusted soy protein slurry is heat-treated at a temperature and for a period of time to effectively denature the soy protein material contained in the soy protein slurry. Denaturation causes the soy protein material to unfold so that more of the insoluble soy protein material will be exposed to enzymatic hydrolysis upon addition of an enzyme to the soy protein slurry. Suitably, the pH-adjusted soy protein slurry is heat-treated at a temperature of between about 70° C. (158° F.) and about 90° C. (194° F.) for a period of time sufficient to denature the soy protein material or putative endogenous protease inhibitors. The pH-adjusted soy protein slurry is heat-treated at a temperature of between about 48° C. (118° F.) and about 55° C. (131° F.), and even more suitably, at a temperature of between about 51° C. (123° F.) and about 53° C. (127° F.). The length of heat-treatment is suitably between about 30 minute and about 70 minutes. More suitably, the length of heat-treatment is between about 35 minutes and about 65 minutes or to optimize the hydrolysis condition. Preferred heat-treatment methods include direct or indirect heating with steam.

After the soy protein material contained in the pH-adjusted soy protein slurry is denatured, an enzyme is added to the pH-adjusted soy protein slurry. The preferred enzyme is an alkaline protease, which is suitably added to the pH-adjusted soy protein slurry at a level of between about 5 mg and about 950 mg or greater enzyme per kilogram of soy protein. The enzyme hydrolysis of the soy protein material at an alkaline pH facilitates two reactions in the pH-adjusted soy protein slurry.

Representative alkaline proteases suitable for use in the processes of the present disclosure include TL1, ALCALASE®, Alkaline Protease Concentrate, and PROTEX™6 L, Bacterial Alkaline Protease. Preferably, the enzyme is TL1.

The time period required for effective enzyme hydrolysis of the soy protein material is typically between about 30 minutes and about 60 minutes. More suitably, enzyme hydrolysis is allowed to occur between about 30 minutes and about 50 minutes, and even more suitably, enzyme hydrolysis is allowed to occur between about 35 and about 45 minutes to optimized time depending on the degree of hydrolysis desired.

During the reaction of the alkaline protease enzyme with the soy protein slurry, the pH is not maintained at a particular level. Rather, it is allowed to fluctuate according to the pH of the alkaline protease enzyme and the chemical processes that occur during the hydrolysis of the soy protein material contained in the pH-adjusted soy protein slurry. Typically, the pH of the resulting enzyme hydrolyzed soy protein mixture will end up at between about 8.0 and about 9.0. After the time period necessary for enzyme hydrolysis is complete, however, the pH of the enzyme hydrolyzed soy protein mixture is adjusted to a pH of between about 7.2 and about 7.6 with a suitable acid. More suitably, the pH of the enzyme hydrolyzed soy protein mixture is adjusted to about 7.4 with a suitable acid. Suitable acids include hydrochloric acid, phosphoric acid, citric acid, and mixtures thereof.

Commercially available hydrolyzed soy protein isolates can be used in the processes of the present disclosure. Suitable hydrolyzed soy protein isolates include SUPRO® XF8020 and SUPRO® XF8021, enzyme hydrolyzed soy protein isolates (Solae, LLC, St. Louis, Mo.).

One skilled in the art will appreciate that it may be desirable to further optimize the soy protein hydrosylate prior to use with the composition of the invention. Such optimization may include, without limitation, separation or impurities, purification of larger fragments from smaller fragments, separation of the soluble phase from the aqueous phase. Methods known in the art may be employed for further optimization, as well as those described in US Patent Application No. 20080182002 and incorporated herein by reference.

(b) Additional Components

Carbohydrates may provide between about 35 and about 65% of the caloric content of the composition. The carbohydrate source may be about 35, 40, 45, 50, 55, 60, 65% or more of the caloric content of the composition. A number of carbohydrates may be used in the present invention. Exemplary carbohydrate sources include, without limitation, maltodextrin, corn starch, sucrose, corn syrup solids, and soy fiber.

The lipid source of the present invention includes a mixture of medium chain triglycerides (MCT). The lipid source may further include a mixture of long chain triglycerides (LCT). Preferably, the lipid source of the composition is between about 20% and about 50% of the caloric content of the total composition. More preferably, the lipid source is between about 25% and about 40% of the caloric content of the total composition. The lipid source may be about 20, 25, 30, 35, 40, 45, 50%, or more of the caloric content of the total composition. The lipid content of the composition is designed to include polyunsaturated fatty acids, such as omega-6 and omega-3 essential fatty acids. Suitable lipid sources include, without limitation, coconut oil, canola oil, corn oil, soybean oil, MCT oil, soy lecithin, residual milk fat, and combinations thereof.

The composition of the present invention also contains the necessary micronutrients for the particular end use application. The necessary micronutrients include vitamins and minerals. While not required, the composition may include 100% or more of the US RDI of vitamins and minerals. The composition may include nutrients within the minimum and maximum range of the EU FSMP requirements for a particular end use application. One skilled in the art will appreciate that the composition may include higher levels of key vitamins and minerals designed to support the needs of the recipient subject. One skilled in the art will recognize that particular ingredients may enhance the recovery of a subject with individual needs and the alteration of key vitamins and minerals depends upon the specialized treatment needed by the subject's condition.

The composition of the present invention may further contain probiotics and other non-nutritive substances that provide physiological benefits. One skilled in the art will appreciate that the composition may include higher levels of key probiotics and other non-nutritive substances designed to support the needs of the recipient subject. One skilled in the art will also recognize that particular ingredients may enhance the recovery of a subject with individual needs and the alteration of key probiotics and other non-nutritive substances depends upon the specialized treatment needed by the subject's condition.

(c) Composition Characteristics

The composition of the present invention may be a ready-to-use enteral formulation. The composition may provide the total nutritional requirements of a metabolically and/or physiologically stressed patient or may act as a supplement. The composition may be tube-fed to a subject, or fed by having the patient drink the formulation. For example, the composition may be provided in cans or a spike and hang bag. The composition may be provided as ready to use without the need for reconstitution or mixing prior to use. Alternatively the composition may be provided such that reconstitution or mixing prior to use is needed.

The present invention may provide calorically dense nutritional support in the form of a liquid diet while at the same time providing a low viscosity formulation with acceptable stability. The viscosity of the composition may measure about 30, 35, 40, 45, 50, 60, 70, 80, 90, 100, 125, 150, and 200 or more centipoises as measured using a viscometer. Preferably, the viscosity is between about 50 and about 150 centipoises. The viscosity of water is about 1 centipoises, while that of molasses is about 100,000 centipoises.

Further, the composition of the invention has the ability to retain stability characteristics following terminal sterilization. As described in the Examples herein, the compositions of the invention retain stability while other formulations develop decreased stability characteristics including bound-sedimentation, flocculation, and phase-separation after terminal sterilization such as retort and ultra high temperature (UHT) treatment.

The compositions of the invention may be designed to meet the nutritional needs of patients suffering from a number of metabolic and/or physiological challenges. The compositions may be further designed to meet the needs of patients with varying fluid, caloric, protein, vitamin and mineral, and/or carbohydrate requirements. The compositions may also be designed to prevent and treat multiple different diseases, including, but not limited to, the following: diarrhea/nausea, irritated bowl disorder, irradiated bowel immunosuppression, pulmonary disease, increased tumor necrosis factor, respiratory failure, sepsis/SIS, multiple organ failure, surgery, cancer, radiation, chemotherapy, wounds, decubiti, stress hyperglycemia, transitional feeding, coronary artery disease, CVA, ischemic reperfusion injury, amputation, malabsorption, gastrointestinal impairment, ulcerative colitis, pancreatitis, metabolic stress, ARDS, COPD, ventilator dependent, pneumonia, hypoperfusion, DIC/symptoms, trauma, cachexia, anorexia, burns, renal dysfunction, long term feeding, CHF, CNS, radiation damage, venous insufficiency, adaptable to renal and/or hepatic failure, Crohn's, bowel resection, glomerulonephritis, critically ill, hypermetabolic, thrombosis, infection, endotoxic shock, abscesses, HIV/AIDS/ARC, diabetes mellitus, liver dysfunction, hypoalbuminemia, cardiogenic shock, gangrene, anemia, dysphagia, and maxillomandibular fixation.

As it will be appreciated, a variety of formulations are possible in accordance with the present invention. By way of example, and not limitation, examples of the suitable compositions that may be used pursuant to the present invention are described in the Examples herein.

(II) Methods

The present invention provides methods utilizing the composition of the invention. In one aspect of the invention, a method of providing nutrition to a subject includes administering to the subject a formulation having an enzymatically hydrolyzed soy protein material, wherein the soy protein material has a degree of hydrolysis of between about 0.1% and about 16%, preferably between about 0.1 and about 5%. The route of administration is enterally including through oral administration, nasogastric administration, gastric feeding tube, duodenal feeding tube, or other digestive system based feeding methods.

Another aspect of the invention includes a method of producing a dietary composition including hydrolyzing a soy protein material such that a soy protein hydrosylate is produced; adding the soy hydrosylate to a heated mixture of lipid ingredients; mixing the soy protein hydrosylate and lipid ingredients to obtain a homogenous slurry; mixing the soy protein hydrosylate and lipid slurry to a slurry of additional ingredients; and homogenizing the resultant mixture. Additional ingredients may include but are not limited to water, carbohydrate sources including dietary fiber sources, lipid sources, salt sources, calcium sources, necessary micronutrients, probiotics and other non-nutritive substances, and combinations thereof. Suitable additional ingredients may include, but are not limited to, water, maltodextrin, corn syrup solids, sugar, sodium caseinate, calcium caseinate, canola oil, medium chain triglyceride oil, soybean oil, potassium citrate, soy fiber, vitamins, minerals, short chain fructo-oligosaccharides, magnesium phosphate, magnesium chloride, sodium chloride, potassium chloride, sodium citrate, lecithin, sodium ascorbate, choline chloride, and combinations thereof.

DEFINITIONS

The term "degree of hydrolysis" (DH) refers to the percent of specific peptide bonds that were hydrolyzed (that is, the number of cleaved out of the number of peptide bonds present in the intact protein).

The terms "endopeptidase" or "peptidase" refer to an enzyme that hydrolyzes internal peptide bonds in oligopeptide or polypeptide chains.

The terms "enteral," "enteral feeding," "enterally," or "enteral administration" refer to the route of delivering nutrients orally, nasogastrically, via gastric feeding tube, via duodenal feeding tube, or through other digestive system based feeding methods known in the art.

A "hydrolysate" is a reaction product obtained when a compound is cleaved through the effect of enzyme. Protein hydrolysates occur subsequent to thermal, chemical, or enzymatic degradation. During the reaction, large molecules are broken into smaller proteins, soluble proteins, peptide fragments, and free amino acids.

The term "necessary micronutrients" as used herein refers to vitamins and minerals in combinations and amounts based on the requirements of a particular end use application.

The term "probiotic" as used herein refers to live microorganisms, which, when administered in adequate amounts, confer a health benefit on the host. (Food Agriculture Organization (FAO) of the United Nations and World Health. *Guidelines for the Evaluation of Probiotics in Food*. Report of a Joint FAO/WHO Working Group on Drafting Guidelines for the Evaluation of Probiotics in food. Accessed Oct. 9, 2009).

The term "purified" as used herein refers to excluding peptides of specific size from the resultant soy hydrosylate. The invention discusses a non-purified soy protein hydrosylate which refers to a hydrosylate such that no peptides generated during the hydrolysis process were excluded from the resultant hydrosylate.

The terms "soy protein isolate" or "isolated soy protein," as used herein, refer to a soy material having a protein content of at least about 90% soy protein on a moisture free basis. A soy protein isolate is formed from soybeans by removing the hull and germ of the soy bean from the cotyledon, flaking or grinding the cotyledon and removing oil from the flaked or ground cotyledon, separating the soy protein and carbohydrates of the cotyledon from the cotyledon fiber, and subsequently separating the soy protein from the carbohydrates.

The term "soy protein concentrate" as used herein is a soy material having a protein content of from about 65% to less than about 90% soy protein on a moisture-free basis. Soy protein concentrate also contains soy cotyledon fiber, typically from about 3.5% up to about 20% soy cotyledon fiber by weight on a moisture-free basis. A soy protein concentrate is formed from soybeans by removing the hull and germ of the soybean, flaking or grinding the cotyledon and removing oil from the flaked or ground cotyledon, and separating the soy protein and soy cotyledon fiber from the soluble carbohydrates of the cotyledon.

The term "soy flour" as used herein, refers to a comminuted form of defatted soybean material, preferably containing less than about 1% oil, formed of particles having a size such that the particles can pass through a No. 100 mesh (U.S. Standard) screen. The soy cake, chips, flakes, meal, or mixture of the materials are comminuted into soy flour using conventional soy grinding processes. Soy flour has a soy protein content of about 49% to about 65% on a moisture free basis. Preferably the flour is very finely ground, most preferably so that less than about 1% of the flour is retained on a 300 mesh (U.S. Standard) screen.

The term "soy cotyledon fiber" as used herein refers to the polysaccharide portion of soy cotyledons containing at least about 70% dietary fiber. Soy cotyledon fiber typically contains some minor amounts of soy protein, but may also be 100% fiber. Soy cotyledon fiber, as used herein, does not refer to, or include, soy hull fiber. Generally, soy cotyledon fiber is formed from soybeans by removing the hull and germ of the soybean, flaking or grinding the cotyledon and removing oil from the flaked or ground cotyledon, and separating the soy cotyledon fiber from the soy material and carbohydrates of the cotyledon.

The term "stability characteristics" as used herein refers to the ability of a composition to remain stable throughout the shelf life of the composition. A decrease in stability characteristics in relation to the compositions of the invention would be indicated by the development sedimentation, flocculation, and phase-separation. Typically, a decrease in stability characteristics occurs in formulations destined for thermal treatments.

"Subject" as used herein typically is a mammalian species. The subject may be a rodent, a human, a livestock animal, a companion animal, or a zoological animal. In one embodiment, the subject is a rodent, i.e. a mouse, a rat, a guinea pig, etc. In another embodiment, the subject is a human. In a yet another embodiment the subject is a livestock animal. Non-limiting examples of livestock animals include pigs, cows, horses, goats, sheep, llamas and alpacas. In still another embodiment, the subject is a companion animal. Non-limiting examples of companion animals include pets, such as dogs, cats, rabbits, and birds. In still yet another embodiment, the subject is a zoological animal. As used herein, a "zoological animal" refers to an animal that may be found in a zoo. Such animals may include non-human primates, large cats, wolves, and bears. In a further embodiments, subjects that may be treated by the methods of the invention include a human, a dog, a cat, a cow, a horse, a rabbit, a pig, a sheep, a goat, as well as non-mammalian species including an avian species and a fish species.

The term "terminal sterilization" as used herein refers to thermal treatment to achieve commercial sterility including retort and aseptically such as ultra high temperature (UHT) treatment.

While the invention has been explained in relation to exemplary embodiments, it is to be understood that various modifications thereof will become apparent to those skilled in the art upon reading the description. Therefore, it is to be understood that the invention disclosed herein is intended to cover such modifications fall within the scope of the appended claims.

In the following tables, the sum of the wt. % of the various components do not add up to 100% exactly because of rounding up or rounding down of the sum of the components.

EXAMPLES

The following examples illustrate various embodiments of the invention.

Example 1

High Caloric Feed Formulation

Enteral feeding formulations can be high caloric density products developed to meet nutritional requirements of enterally-fed subjects. enteral feed formulas are administered orally, via gravity, or using a pump, therefore, viscosity and stability of the finished product over the shelf life are critical in terms of meeting the targeted quantity and duration of the feeding regiment. Typical issues associated with dairy and soy protein ingredients when used in enteral feeding formulations include high initial viscosity or viscosity build-up over time as the inclusion level increases. Enzyme-treated dairy and soy protein ingredients may help to alleviate the viscosity challenges.

Figure 1:
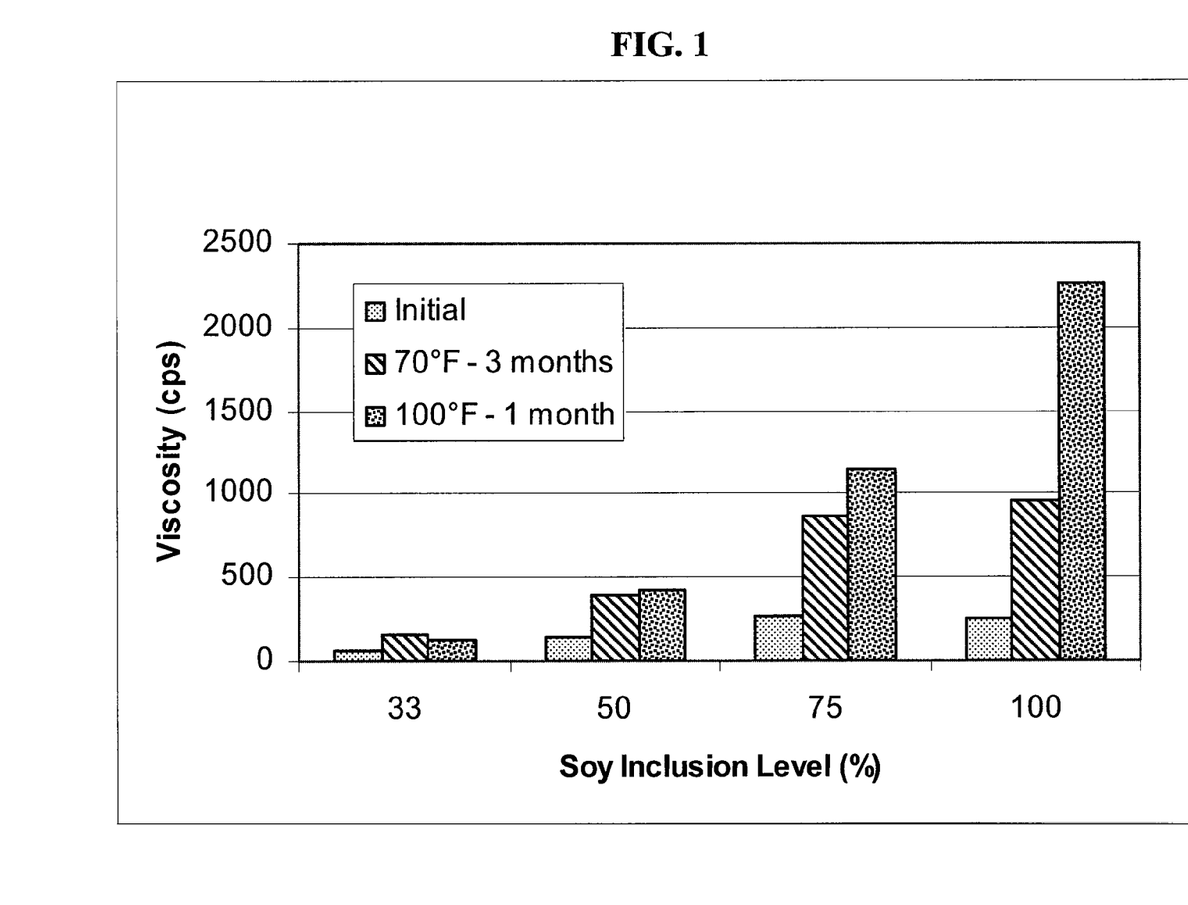
FIG. 1 graphically illustrates the viscosity of soy containing formulations.
Figure 2:
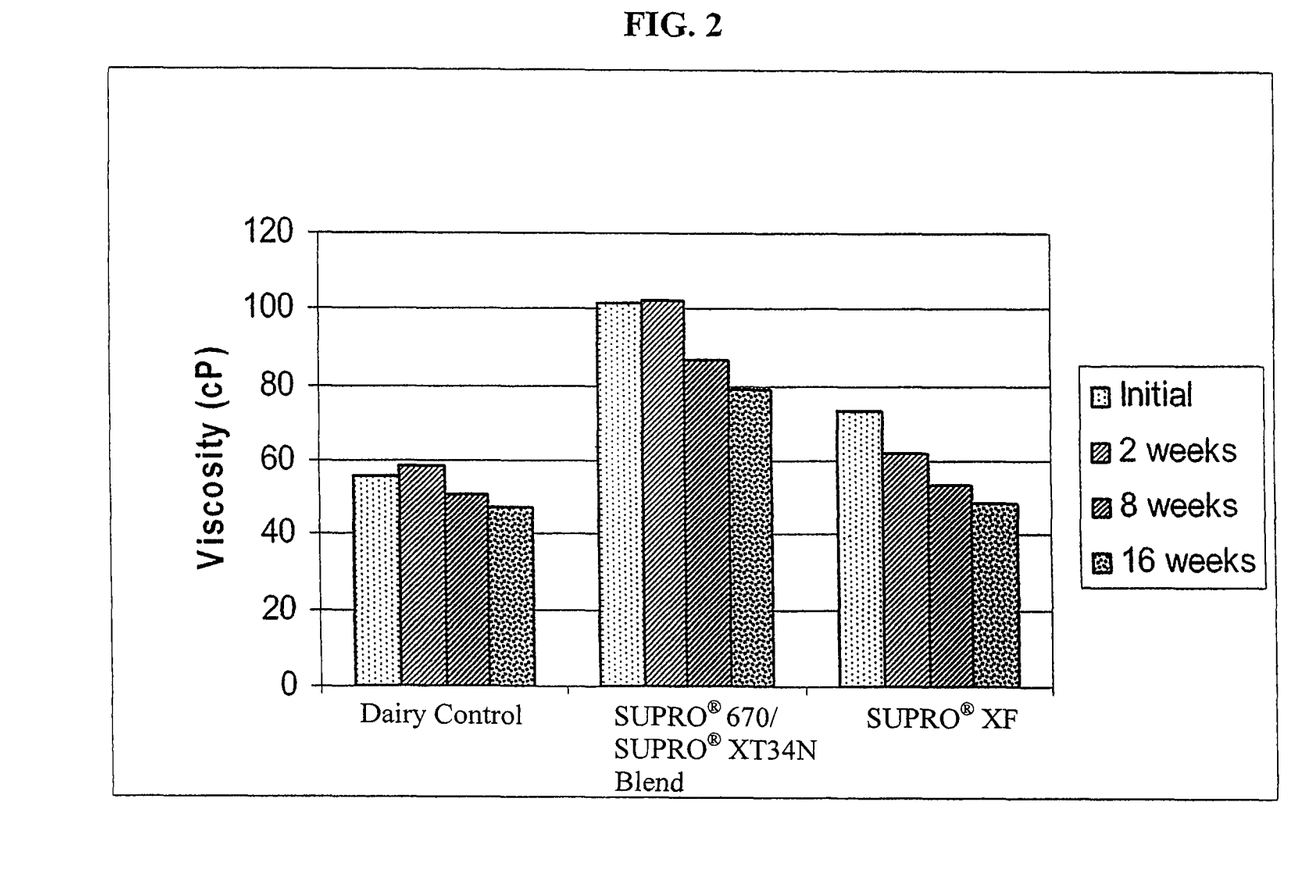
FIG. 2 graphically illustrates the viscosity of soy containing formulations having 50% soy inclusion of variously treated soy compositions.

In order to determine an optimum soy inclusion level at which there is no significant increase in viscosity, a non-optimized high caloric feed formulation was used to produce sample prototypes with varying soy inclusion levels (33%, 50%, 75%, and 100%) (FIG. 1). The formulation used to determine the optimum soy inclusion level is shown in Table 1.

TABLE 1

Formulation Used for determining optimum soy inclusion level.

| Ingredients | Percentage use (%) |
| --- | --- |
| Water | 70.6-71.1 |
| Maltodextrin | 7.6 |
| Sugar | 6.4 |
| Sodium and Calcium caseinate | 0-4 |
| Canola oil | 2.5 |
| MCT oil (medium chain triglycerides) | 1.9 |
| Soy protein isolate SUPRO ® 1610 | 2.2-6.7 |
| Soy bean oil | 1.4 |
| Potassium citrate | 0.3 |

TABLE 1-continued

Formulation Used for determining optimum soy inclusion level.

| Ingredients | Percentage use (%) |
| --- | --- |
| Fiber | 1.0 |
| Vitamin/Mineral premix | 0.5 |
| Magnesium chloride | 0.3 |
| Sodium chloride | 0.1 |
| Potassium chloride | 0.2 |
| Sodium citrate | 0.2 |
| Lecithin | 0.1 |
| Sodium ascorbate | 0.09 |
| Choline chloride | 0.08 |

Citrates and magnesium salts were added to 80-98% of the water at 77° C. (170° F.) and mixed. The sodium and calcium caseinates were added and disperse quickly and mixed for 10 minutes. Carbohydrates (fiber, maltodextrin, corn syrup solids and sugar) were added to the caseinate mix and mixed for 5 minutes. In a second tank, the canola, soybean oil and lecithin were mixed and heated to 74° C. (165° F.). For preparation of the soy containing samples, the soy protein was added to the oil after heating and mixed until obtaining a homogenous sample. After mixing, MCT oil was added. The oil-protein slurry was added to the caseinates slurry and mixed until all ingredients were dissolved (5-10 minutes). The pH of slurry was measured and adjusted to 7.0-7.1 using 45% potassium hydroxide. The resulting mixture was homogenized to 3000-3500 psi total. Minerals were dissolved in 1-10% of the water and added to the homogenized mixture. Product was homogenized to 3000-3500 psi total. Sodium ascorbate was dissolved in 1-10% of the remaining water and added to the homogenized slurry. Product was collected in cans and retorted to 121° C.-122° C. (250° F.-252° F.) for 10 minutes. Samples were evaluated for pH, viscosity, color and stability over a specific period of time.

As the level of inclusion dairy protein decreased and soy protein increased, the viscosity and stability characteristics were affected. Specifically, in this case, as the level of soy inclusion increased (especially at 75% and 100% soy inclusion), the viscosity increased considerably after 3 months at 21° C. (70° F.). Data indicated that when samples were submitted to accelerated storage conditions at 37° C. (100° F.) for 1 month, there was viscosity build up at 75% and 100% soy inclusion. Viscosity of 33% and 50% samples did not change dramatically under elevated temperature storage (FIG. 1). The results indicated that with the available ingredients, 50% inclusion level of soy protein is likely the optimal concentration which would yield acceptable viscosity and shelf life stability in subsequent formulations.

Example 2

Evaluation of Sample Formulations

A novel enzyme-treated soy protein that is characterized by exhibiting low viscosity and good solubility was used to replace a significant amount of the total dairy protein found in higher caloric enteric nutrition formulas (1.5 kcal/ml) to obtain a product with both low viscosity and acceptable stability. The high caloric sample feed formulations are detailed in Table 2.

TABLE 2

High Caloric Feed Formulation

| Ingredients | Control-100% Dairy (Sample 1) Percentage use (%) | 50:50 Dairy:SUPRO ® 670/SUPRO ® XT34N blend (Sample 2) Percentage use (%) | 50:50 Dairy:SUPRO ® XF (Sample 3) Percentage use (%) |
| --- | --- | --- | --- |
| Water | 70.9 | 70.5 | 70.7 |
| Maltodextrin | 7.6 | 0.0 | 0.0 |
| Corn syrup solids | 0.0 | 9.5 | 9.5 |
| Sugar | 6.4 | 4.4 | 4.4 |
| Sodium and Calcium caseinate | 6.7 | 3.4 | 3.4 |
| Canola oil | 2.5 | 2.5 | 2.5 |
| Medium chain triglycerides (MCT oil) | 1.9 | 1.9 | 1.9 |
| Soy protein isolate SUPRO ® 670 | 0.0 | 1.7 | 0.0 |
| Soy protein isolate SUPRO ® XT34N | 0.0 | 1.8 | 0.0 |
| Soy protein isolate SUPRO ® XF | 0.0 | 0.0 | 3.3 |
| Soybean oil | 1.4 | 1.4 | 1.4 |
| Potassium citrate | 0.3 | 0.5 | 0.5 |
| Fiber | 1.0 | 1.0 | 1.0 |
| Vitamin Mineral Premix | 0.5 | 0.5 | 0.5 |
| Magnesium Phosphate, dibasic | 0.0 | 0.2 | 0.2 |
| Magnesium chloride | 0.3 | 0.0 | 0.0 |
| Sodium chloride | 0.0 | 0.1 | 0.1 |
| Potassium chloride | 0.0 | 0.2 | 0.2 |
| Sodium citrate | 0.2 | 0.1 | 0.1 |
| Lecithin | 0.1 | 0.1 | 0.1 |
| Sodium ascorbate | 0.09 | 0.09 | 0.09 |
| Choline chloride | 0.08 | 0.08 | 0.08 |

Three prototypes were made for evaluation including a control sample containing 100% dairy protein (Sample 1), a blend of commercially available soy protein (Sample 2), and an enzyme-treated soy sample (Sample 3). Citrates and magnesium salts were added to 80-98% of the water at 77° C. (170° F.) and mixed. The sodium and calcium caseinates were added and dispersed quickly and mixed for 10 minutes. Carbohydrates (fiber, maltodextrin, corn syrup solids, and sugar) were added to the caseinate mix and mixed for 5 minutes. In a second tank, the canola, soybean oil and lecithin were mixed and heated to 74° C. (165° F.). For preparation of the soy containing samples, the soy protein was added to the oil after heating and mixed until obtaining a homogenous sample. After mixing, MCT oil was added. The oil-protein slurry was added to the caseinates slurry and mixed until all ingredients were dissolved (5-10 minutes). The pH of slurry was measured and adjusted to 7.0-7.1 using 45% potassium hydroxide. The resulting mixture was homogenized to 3000-3500 psi total. Minerals were dissolved in 1-10% of the water and added to the homogenized mixture. Product was homogenized to 3000-3500 psi total. Sodium ascorbate was dissolved in 1-10% of the remaining water and added to the homogenized slurry. Product was collected in cans and retorted to 121° C.-122° C. (250° F.-252° F.) for 10 minutes. Samples were evaluated for pH, viscosity, color and stability over a specific period of time.

The samples (Table 2) were evaluated for pH, viscosity, color, and stability over a specific period of time.

pH

The pH measurement of the samples was performed following standard procedures. The pH of the control sample ranged from about 6.8 to 6.9 and the soy-containing samples ranged from about 6.6 to 6.7. The pH of all products did not change considerably over time. It remained stable over the evaluation of shelf life (Table 3).

TABLE 3 pH of Sample Formulations.

| Sample ID | Sample | Initial | 2 weeks | 8 weeks | 16 weeks |
|---|---|---|---|---|---|
| 1 | 100% Dairy protein | 6.9 | 6.8 | 6.9 | 6.9 |
| 2 | SUPRO ® 670/ SUPRO ® XT34N blend | 6.6 | 6.6 | 6.7 | 6.7 |
| 3 | SUPRO ® XF | 6.7 | 6.7 | 6.7 | 6.7 |

Viscosity

The viscosity of the sample formulations was measured using a viscometer. Specifically, the samples were shaken to achieve a uniform dispersion and immediately poured into a 180 ml beaker. Any visible foam was removed before measurement. After the fixed time period had elapsed, the viscosity was measured in centipoises (cP) using a Brookfield viscometer (model DV-II+) with spindle #2 and RPM 30 for 1 minute at 25° C. to 30° C. (77° F. to 86° F.). Results can be seen in Table 4.

Typically, enzyme-treated soy proteins are characterized by exhibiting low viscosity but poor stability, especially when submitted to retort processing conditions. Nonetheless, in general, the sample made with the novel enzyme-treated soy protein showed comparable stability to the control (100% dairy proteins) and was more stable than the blend of commercially available soy proteins (Table 4).

TABLE 4

Viscosity of Sample Formulations.

| Sample ID | Sample | Initial | 2 weeks | 8 weeks | 16 weeks |
|---|---|---|---|---|---|
| 1 | 100% Dairy protein | 56.0 | 58.5 | 51.0 | 47.0 |
| 2 | SUPRO ® 670/ SUPRO ® XT34N blend | 101.5 | 102.5 | 86.5 | 79.0 |
| 3 | SUPRO ® XF | 73.5 | 62.0 | 54.0 | 48.5 |

Color

The color of the sample formulations was measured using a HunterLab Colorimeter (Model DP-9000). The instrument was calibrated following standard procedures. Samples were shaken to achieve uniform dispersion. The temperature of the samples was about 25° C.-30° C. (77° F.-86° F.). Equal amounts of each sample were poured into sample cups (Agtron 57 mm I.D. Glass Catalog No. 11595, Magnuson Engineering, Inc.) and any trapped air bubbles were removed. The filled sample cup was placed over the instrument measurement port and covered. Samples were read and the results were recorded in units of L, a, and b.

The color of soy-containing samples differed from the 100% dairy sample as expected (Table 5). However, the L value, indicating the lightness or whiteness, for all samples, remained constant throughout the shelf life study.

TABLE 5

Color of Sample Formulations

| Sample ID | Sample | Lightness (L) | | | | A | | | | b | | | |
|---|---|---|---|---|---|---|---|---|---|---|---|---|---|
| | | 0 wk | 2 wk | 8 wk | 16 wk | 0 wk | 2 wk | 8 wk | 16 wk | 0 Wk | 2 wk | 8 wk | 16 wk |
| 1 | 100% Dairy protein | 66.5 | 66.4 | 66.8 | 66.0 | 4.1 | 4.3 | 3.6 | 4.0 | 17.9 | 18.1 | 17.6 | 17.8 |
| 2 | SUPRO ® 670/ SUPRO ® XT34N blend | 61.6 | 60.9 | 61.0 | 60.2 | 6.6 | 7.0 | 6.6 | 6.7 | 20.0 | 20.3 | 19.9 | 19.8 |
| 4 | SUPRO ® XF | 61.1 | 60.7 | 60.2 | 59.8 | 6.5 | 6.9 | 6.1 | 6.5 | 19.9 | 20.4 | 19.3 | 19.7 |

Stability

The stability of the formulations was assessed at 0, 2, and 8 weeks shelf life (Table 7). Undisturbed product cans for each sample were opened and visually inspected for creaming, serum, sedimentation, and particulates. Once opened, the appearance of the top layer of the beverage was subjectively evaluated for creaming and particulates. The sample was then poured and examined for serum and sediment. The samples were assigned a score to describe their stability based on the internally developed scale shown in Table 6.

TABLE 6

Stability scale.

| Score | Description |
|---|---|
| 1 | Heavy particulates, product break apart, layer separation and/or hard to shake back sediment |
| 2 | Considerable amount of particulates, creaming, serum and/or sediment, moderately easy to shake back sediment |
| 3 | Minimum particulates, creaming, serum and/or sedimentation, easy to shake back sediment |
| 4 | No defects detected, homogenous product |

TABLE 7

Stability Evaluation of Sample Formulations.

| | | Stability Score | | |
|---|---|---|---|---|
| Sample ID | Sample | initial | 2 wk | 8 wk |
| 1 | 100% Dairy protein | 4 | 3 | 3 |
| 2 | SUPRO ® 670/ SUPRO ® XT34N blend | 4 | 2 | 2 |
| 3 | SUPRO ® XF | 4 | 3 | 3 |

The stability of Sample 3 was comparable to Sample 1, the control, having 100% dairy protein.

Overall, Sample 3 exhibited a viscosity comparable to Sample 1, the dairy control sample after 16 weeks (Table 4).

Example 3

Comparison of Existing Soy Protein Technology and the Novel Enzyme-Treated Soy Protein in the High Caloric Feed Formulation High caloric feed formulations containing 100% of the total protein derived from soy were prepared using similar procedure as in Example 1. Formulas were modified to optimize the sequestrant agents as to maximize stability and to provide similar mineral profile among the samples, regardless of the protein source used. Commercially sterilized products were transferred to sterile clear plastic bottles to evaluate stability over time (Table 8).

TABLE 8

Modified High Caloric Feed Formulation

| Ingredients | 100% SUPRO ® XF (Sample 1) Percentage use (%) | 100% SUPRO ® 670 (Sample 2) Percentage use (%) |
|---|---|---|
| Water | 70.3 | 70.3 |
| Corn syrup solids | 9.7 | 9.7 |
| Sugar | 4.6 | 4.6 |
| Canola oil | 2.6 | 2.6 |
| Medium chain triglycerides (MCT oil) | 2.0 | 2.0 |
| Soy protein isolate SUPRO ® 670 | 0.0 | 7.2 |
| Soy protein isolate SUPRO ® XF | 7.2 | 0.0 |
| Soybean oil | 1.4 | 1.4 |
| Potassium citrate | 0.4 | 0.4 |
| Fiber | 1.0 | 1.0 |
| Vitamin/Mineral premix | 0.06 | 0.06 |
| Magnesium Phosphate, dibasic | 0.3 | 0.3 |
| Sodium chloride | 0.1 | 0.0 |
| Potassium chloride | 0.03 | 0.2 |
| Sodium citrate | 0.1 | 0.1 |
| Lecithin | 0.1 | 0.1 |
| Choline chloride | 0.07 | 0.07 |

The finished products were stored at room temperature and evaluated for pH, physical stability and viscosity at 1 day, 2 and 4 weeks shelf life following similar procedures as in Example 2.

TABLE 9 pH of sample formulations

| Sample ID | Sample | Initial | 2 weeks | 4 weeks |
|---|---|---|---|---|
| 1 | 100% SUPRO ® XF | 7.0 | 6.9 | 6.9 |
| 2 | 100% SUPRO ® 670 | 7.0 | 7.0 | 7.0 |

The pH of all products did not change considerably over time. It remained stable over the evaluation of shelf life.

TABLE 10

Viscosity of Sample Formulations

| Sample ID | Sample | Initial | 2 weeks | 4 weeks |
|---|---|---|---|---|
| 1 | 100% SUPRO ® XF | 117 | 153 | 150 |
| 2 | 100% SUPRO ® 670 | 138 | 153 | 158 |

Viscosity evaluation of the Samples indicated that the soy containing Samples had an increased viscosity after two weeks, but the viscosity remained constant at 4 weeks shelf life for both Samples. Despite both Samples having similar viscosity at a targeted time, Samples differed in their stability. Sample 2 exhibited heavy aggregates upon retort thermal process whereas, Sample 1 had minimum aggregates, creaming, and sediment after 4 weeks.

Example 4

High Caloric Feed Formulation

Enteral feeding formulations can be high caloric density products developed to meet nutritional requirements of enterally-fed subjects. Enteral feed formulas are administered orally, via gravity or using a pump, therefore, viscosity and stability of the finished product over the shelf life is critical in terms of meeting the targeted quantity and duration of the feeding regiment. Typical issues associated with dairy and soy protein ingredients when used in enteral feeding formulations include high initial viscosity or viscosity build-up over time as the inclusion level increases. Enzyme-treated dairy and soy protein ingredients may help to alleviate the viscosity challenges.

Similar formulations as described in Example 3 can be used to produce sample prototypes with varying soy inclusion levels (33%, 50%, 75%, and 100%) that can be heat treated by means of ultra-high temperature (UHT) process. Certain ingredients usage levels like vitamins and minerals can be adjusted as their exposure to heat treatment to achieve commercial sterility is lowered, therefore reducing the need to add increased amounts to compensate for the loss during significant exposure to heat treatment (Table 11).

TABLE 11

Formulation for producing high caloric feed formulations.

| Ingredients | 100% SUPRO ® XF Percentage use (%) |
|---|---|
| Water | 70.3 |
| Corn syrup solids | 9.7 |
| Sugar | 4.6 |
| Canola oil | 2.6 |
| MCT oil (medium chain triglycerides) | 2.0 |
| Soy protein isolate, SUPRO ® 670 | 7.2 |
| Soy protein isolate, SUPRO ® XF | 0.0 |
| Soy bean oil | 1.4 |
| Potassium citrate | 0.4 |
| Fiber | 1.0 |
| Vitamin/Mineral premix | 0.06 |
| Magnesium Phosphate, dibasic | 0.3 |
| Sodium chloride | 0.1 |
| Potassium chloride | 0.03 |
| Sodium citrate | 0.1 |
| Lecithin | 0.1 |
| Choline chloride | 0.07 |

Add citrates and magnesium salts to 80-98% of the water at 77° C. (170° F.) and mix. Add the sodium and calcium caseinates and disperse quickly and mix for 10 minutes. Add carbohydrates (fiber, maltodextrin, corn syrup solids and sugar) to the caseinate mix and mix for 5 minutes. In a second tank, mix the canola, soybean oil and lecithin and heat to 74° C. (165° F.). For preparation of the soy containing samples, add the soy protein to the oil after heating and mix until a homogenous sample is obtained. After mixing, add MCT oil. Add the oil-protein slurry to the caseinates slurry and mix until all ingredients are dissolved (5-10 minutes). Measure the pH of the slurry and adjust the pH to 7.0-7.1 using 45% potassium hydroxide. Homogenize the resulting mixture to 3000-3500 psi total. Dissolve vitamins and minerals in 1-10% of the water and add to the homogenized mixture. Homogenize the product to 3000-3500 psi total. The product is aseptically treated by ultra-high temperature (UHT) processing at 141° C. (286° F.) for 6 seconds and collected in sterile plastic bottles. Flavor can be added to make an orally digestible formula.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the claims.

What is claimed is:

1. A dietary composition having a caloric density of 1.4 kcal/ml to about 2.1 kcal/ml, a low viscosity ranging from about 30 to 200 centipoises, and capability to retain stability characteristics following terminal sterilization, the composition comprising:
   a. enzymatically hydrolyzed soy protein material, wherein the soy protein material has a degree of hydrolysis of between about 0.1% and about 16%;
   b. a carbohydrate source wherein the carbohydrate source provides at least about 35% of the caloric content of the composition;
   c. a lipid source; and
   d. necessary micronutrients.

2. The dietary composition of claim 1, wherein the soy protein material has a degree of hydrolysis of between about 0.1% and about 5%.

3. The dietary composition of claim 1, wherein the composition is a liquid.

4. The dietary composition of claim 1, wherein the necessary micronutrients are selected from the group consisting of 100% of U.S. RDI of vitamins and minerals or more than 100% United States Reference Daily Intake of vitamins and minerals.

5. The dietary composition of claim 1, wherein the composition further includes nutrients within the minimum and the maximum range of the European Union Foods for Special Medical Purposes (EU FSMP) requirements for a particular end use application.

6. The dietary composition of claim 1, wherein the soy protein material is selected from the group consisting of soy protein, soy protein isolate, soy protein concentrate, soy protein extract, soy flour, powdered or dry soy milk, soy meal, ground soy bean, soy bean paste, and combinations thereof.

7. The dietary composition of claim 1, wherein the viscosity is between about 30 and about 110 centipoises.

8. The dietary composition of claim 1, wherein the viscosity is between about 50 and about 150 centipoises.

9. The dietary composition of claim 1, wherein the carbohydrate source is selected from the group consisting of maltodextrin, corn syrup solids, sugar, soy fiber, short chain fructooligosacharides, or combinations thereof.

10. The dietary composition of claim 1, wherein the lipid source is selected from the group consisting of canola oil, medium chain triglycerides, soybean oil, or combinations thereof.

11. The dietary composition of claim 1, further including ingredients selected from the group consisting of water, salt sources, calcium sources, probiotics, and combinations thereof.

12. A method of providing nutrition to a subject in need thereof, the method comprising administering to the subject a formulation having a caloric density of 1.4 kcal/ml to about 2.1 kcal/ml, a low viscosity ranging from about 30 to 200 centipoises, and capability to retain stability characteristics following terminal sterilization, the composition comprising:
   a. enzymatically hydrolyzed soy protein material, wherein the soy protein material has a degree of hydrolysis of between about 0.1% and about 16%;

b. a carbohydrate source wherein the carbohydrate source provides at least about 35% of the caloric content of the composition;
c. a lipid source; and
d. necessary micronutrients.

13. The method of claim 12, wherein the method of providing nutrition to a subject is enteral administration.

14. The method of claim 12, wherein the formulation includes necessary micronutrients selected from the group consisting of 100% of U.S. RDI of vitamins and minerals or more than 100% US RDI of vitamins and minerals.

15. The method of claim 12, wherein the formulation includes nutrients within the minimum and the maximum range of the EU FSMP requirements for a particular end use application.

16. The method of claim 12, wherein the soy protein material is selected from the group consisting of soy protein, soy protein isolate, soy protein concentrate, soy protein extract, soy flour, powdered or dry soy milk, soy meal, ground soy bean, soy bean paste, and combinations thereof.

17. The method of claim 12, wherein the viscosity is between about 30 and about 110 centipoises.

* * * * *